(12) United States Patent
Yang

(10) Patent No.: US 10,231,935 B1
(45) Date of Patent: Mar. 19, 2019

(54) PROCESS FOR MANUFACTURING PULLULAN HARD CAPSULES HAVING IMPROVED FILM PROPERTIES

(71) Applicant: SUHEUNG CO., LTD., Chungbuk (KR)

(72) Inventor: Joo-Hwan Yang, Gyeonggi-do (KR)

(73) Assignee: SUHEUNG CO., LTD., Chungbuk (KR)

( * ) Notice: Subject to any disclaimer, the term of this patent is extended or adjusted under 35 U.S.C. 154(b) by 0 days.

(21) Appl. No.: 15/880,995

(22) Filed: Jan. 26, 2018

(30) Foreign Application Priority Data

Nov. 7, 2017 (KR) .......................... 10-2017-0147289

(51) Int. Cl.
| | |
|---|---|
| *A61J 3/07* | (2006.01) |
| *A61K 9/48* | (2006.01) |
| *A61K 47/36* | (2006.01) |
| *A61K 31/167* | (2006.01) |

(52) U.S. Cl.
CPC ............... *A61K 9/4833* (2013.01); *A61J 3/07* (2013.01); *A61K 9/4816* (2013.01); *A61K 31/167* (2013.01); *A61K 47/36* (2013.01)

(58) Field of Classification Search
None
See application file for complete search history.

(56) References Cited

FOREIGN PATENT DOCUMENTS

| | | |
|---|---|---|
| EP | 2663294 B1 | 9/2015 |
| WO | 01/07507 A1 | 2/2001 |

*Primary Examiner* — Susan T Tran
*Assistant Examiner* — William Craigo
(74) *Attorney, Agent, or Firm* — MH2 Technology Law Group, LLP

(57) ABSTRACT

The present invention relates to a process for manufacturing pullulan hard capsules having improved film properties. More particularly, the present invention relates to a process for manufacturing pullulan hard capsules having improved film properties by solving the problems, such as, sticky among pullulan hard capsules, storage stability and/or brittleness.

5 Claims, 2 Drawing Sheets

PROCESS FOR MANUFACTURING PULLULAN HARD CAPSULES HAVING IMPROVED FILM PROPERTIES

TECHNICAL FIELD

The present invention relates to a process for manufacturing pullulan hard capsules having improved film properties. More particularly, the present invention relates to a process for manufacturing pullulan hard capsules having improved film properties by solving the problems, such as, sticky among pullulan hard capsules, storage stability and/or brittleness.

DESCRIPTION OF PRIOR ART

Pullulan is a safe and non-animal derived polysaccharide obtained by isolating and purifying polysaccharides produced from black yeast, especially, *Aureobasidium pullulans*. Further, the pullulan capsules are suitable for filling oils prone to be acidified due to the low oxygen permeability. Also, the pullulan capsules seldom result in the Maillard reaction by the redox phenomenon even after filling vitamin C. Therefore, it has been commercialized as a safe hard capsule base material compared to gelatin derived from animal origins.

Since the pullulan hard capsule has following physicochemical properties, it has been regarded as capsule replacing the gelatin hard capsule.

Pullulan is a non-animal derived material showing very low oxygen permeability and high transparency without chemical degradation. When pullulan is added to cold or hot water, it can be easily disintegrated without any residue. Therefore, pullulan has been recognized as a safe material without cross-linkage in these macromolecules.

On the other hand, since a pullulan film has a relatively high viscosity and/or tackiness, sticky and/or storage stability problems among pullulan hard capsules can be raised. Further, a pullulan film has a relatively low water content, which also causes brittleness problems due to the insufficient film strength when hygroscopic material is filled.

PCT Int'l Pub. No. WO 2001/007507 'pullulan film composition' disclosed a pullulan film composition comprising 85-95 wt % of pullulan and 5-15 wt % of a setting system.

In this patent disclosure, at least one hydrocolloids of the setting system selected from alginates, agar gum, guar gum, locust bean gum (carob), carrageenan, tara gum, gum arabic, ghatti gum, kaya *grandifolia* gum, tragacanth gum, karaya gum, pectin, arabian (araban), xanthan, gellan, starch, konjac mannan, galactomannan or funoran has been disclosed. Further, at least one metal cations selected from $K^+$, $Na^+$, $Li^+$, $NH_4^+$, $Ca^{2+}$ or $Mg^{2+}$ has been also disclosed as gelling aid.

On the other hand, in this patent disclosure, it has been described that a pullulan hard capsule can have a relatively high viscosity and/or tackiness, which can raise sticky and/or storage stability problems among pullulan hard capsules. For solving these problems, it has been disclosed that at least one surfactant selected from sodium lauryl sulfate (SLS), dioctyl sodium sulfosuccinate (DSS), benzalkonium chloride, benzethonium chloride, cetrimide, fatty acid saccharide esters, glyceryl monooleate, polyoxyethylene sorbitan fatty acid esters, polyvinyl alcohol, dimethyl polysiloxan, sorbitan esters or lecithin has to be included in a pullulan film composition.

However, even if at least one surfactant is included in a pullulan film composition, the sticky problem among pullulan hard capsules cannot be fully prevented due to the high tackiness of pullulan hard capsule resulted from high viscosity of aqueous pullulan solution at the dip-molding temperature.

On the other hand, in European Patent No. 2,663,294 B1 'New hard capsules comprising pullulan', a novel pullulan hard capsule composition for preventing brittleness caused by insufficient film strength of pullulan hard capsules has been disclosed.

In this patent disclosure, a pullulan hard capsule comprising lower than amount of 2.5 wt % of mono-, di- and oligo-saccharide, which is manufactured by mono-, di- and oligo-saccharide free pullulan as a raw material, has been disclosed for preventing brittleness by improving film strength of pullulan hard capsules.

Even though the brittleness of pullulan hard capsules can be partly prevented by producing pullulan hard capsules using mono-, di- and oligo-saccharide free pullulan as a raw material, the dissolution problem can be raised due to the uneven film strength and/or distribution. Further, the disintegration of pullulan hard capsules cannot be also improved compared to conventional pullulan hard capsules due to the uneven film strength and/or distribution.

To improve the sticky and/or storage stability due to high tackiness along with the brittleness due to low water content and uneven film strength, the inventor of present invention has developed a process for manufacturing pullulan hard capsules having improved film properties. Further, the pullulan hard capsules of present invention also show a sufficient dissolution property of filled ingredients with a rapid disintegration property of pullulan hard capsules.

To afford the pullulan hard capsule having improved film properties, the inventor of present application has adopted iota-carrageenan as gelling agent in combination with potassium carbonate and magnesium chloride as auxiliary gelling agent, polyglycerin fatty acid ester as emulsifying agent for reducing the high tackiness of pullulan film, and colloidal silica as viscosity stabilizer to adjust the viscosity of pullulan aqueous mixture at 57° C. to be 0.7-1.5 Pa·s.

Accordingly, the pullulan hard capsule having improved film properties of present invention has been completed by solving the sticky, storage stability and/or brittleness problem. Further, the pullulan hard capsule of present invention can provide the improved dissolution of filled ingredients with the improved disintegration of pullulan hard capsule shell.

Problem to be Solved

The problem to be solved is to develop a pullulan hard capsule having improved film properties by solving the sticky and/or storage stability problem caused by high tackiness along with the brittleness problem caused by low water content and uneven film strength and/or distribution.

Means for Solving the Problem

The object of present invention is to provide a process for preparing a pullulan hard capsule having improved film properties comprising the steps of: i) sequentially adding and solubilizing 0.01-0.2 wt part of propylene glycol as plasticizing agent, 0.001-0.02 wt part of polyglycerin fatty acid ester as emulsifying agent, 0.01-0.2 wt part of colloidal silica as viscosity stabilizer, and 18-22 wt part of pullulan to the 80 wt part of purified water at 77-83° C.; ii) sequentially adding and solubilizing 0.3-1.0 wt part of iota-carrageenan as gelling agent, 0.03-0.3 wt part of potassium carbonate and 0.05-0.3 wt part of magnesium chloride as auxiliary gelling agent; and 0.001-0.05 wt part of glacial acetic acid as a pH neutralizing agent to the resulting admixture, after cooling the obtained mixture in step i) at 57-63° C.; iii) transferring the resulting admixture to the dipping pan at 57-63° C. after adjusting the viscosity of the mixture obtained in step ii) to be 0.7-1.5 Pa·s at 57° C., forming a pullulan hard capsule using mold pin, and cooling and drying a pullulan hard capsule using 15-35° C. air for 40-70 minutes; wherein said forming step comprises a) adjusting the temperature of mold pin to 20-25° C., b) dipping the mold pin into the dipping pan at constant velocity, and c) withdrawing the mold pin from the dipping pan at accelerated velocity and subsequently at reduced velocity for 16-18 seconds.

Further, the weight average molecular weight of pullulan is 150-300 kDa.

Further, said iota-carrageenan as gelling agent can concretely gelate the pullulan hard capsule in collaborate with $K^+$ cation in potassium carbonate and $Mg^{2+}$ cation in magnesium chloride.

Further, said colloidal silica as viscosity stabilizer is used to adjust the viscosity of pullulan aqueous mixture to be 0.7-1.5 Pa·s at 57° C., which is a stable spherical particle of fumed silica having 99.0-100.5 wt % of $SiO_2$ content, pH 3.5-5.5 at 4 wt % aqueous solution The other object of present invention is to provide a pullulan hard capsule having improved film properties prepared by said process, wherein the dissolution profile of acetaminophen at 30 minutes shows more than 70 wt % of dissolution in purified water (pH 7.0) according to the paddle method of dissolution test in Korean pharmacopoeia 10th Edition.

Advantageous Effect

The outstanding advantageous effect of the present invention is to provide a pullulan hard capsule having improved film properties by solving the sticky and/or storage stability problem caused by high tackiness along with the brittleness problem caused by low water content and uneven film strength and/or distribution. Further, a pullulan hard capsule having improved dissolution of filled ingredients as well as the improved disintegration of pullulan hard capsule shell also can be provided.

t1 represents pin bars transferring for dipping, t2 represents mold pin down at constant velocity, t3 represents mold pin withdrawal at accelerated velocity, t4 represents mold pin withdrawal at reduced velocity, and t5 represents pin bars transferring after withdrawal.

Figure 3:
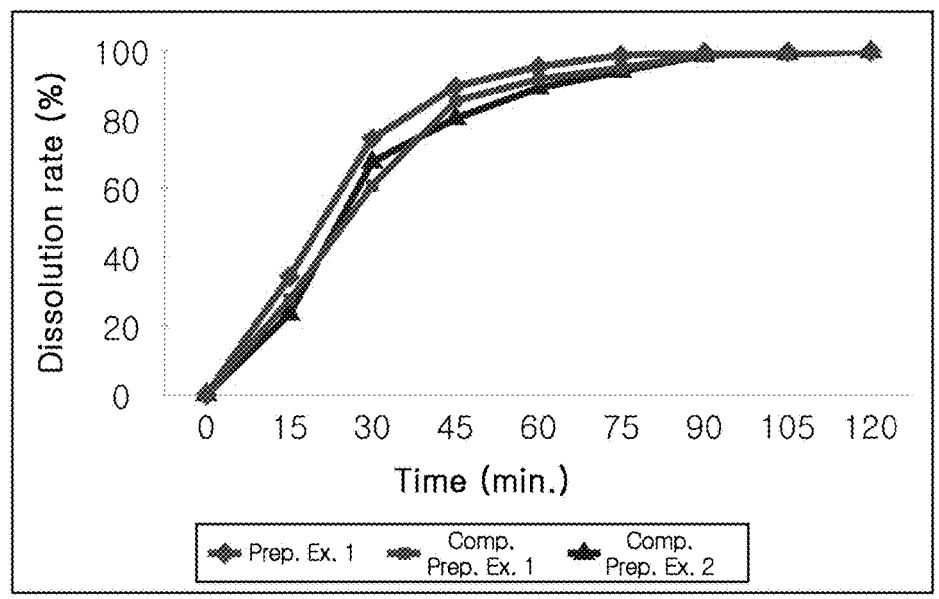

FIG. 3 is a diagram showing dissolution profile of acetaminophen in purified water (pH 7.0) for 120 minutes according to the paddle method of dissolution test in Korean pharmacopoeia 10th Edition. Pullulan hard capsule prepared in Preparation Example 1, Comparative Preparation Example 1 and Comparative Preparation Example 2 have been used for measuring dissolution profile after filling acetaminophen.

The dissolution profile of acetaminophen of Preparation Example 1 in present invention shows more than 70 wt % of dissolution in purified water (pH 7.0) at 30 minutes according to the paddle method of dissolution test in Korean pharmacopoeia 10th Edition.

PREFERRED EMBODIMENT OF INVENTION

The present invention relates to a process for preparing a pullulan hard capsule having improved film properties comprising the steps of: i) sequentially adding and solubilizing 0.01-0.2 wt part of propylene glycol as plasticizing agent, 0.001-0.02 wt part of polyglycerin fatty acid ester as emulsifying agent, 0.01-0.2 wt part of colloidal silica as viscosity stabilizer, and 18-22 wt part of pullulan to the 80 wt part of purified water at 77-83° C.; ii) sequentially adding and solubilizing 0.3-1.0 wt part of iota-carrageenan as gelling agent, 0.03-0.3 wt part of potassium carbonate and 0.05-0.3 wt part of magnesium chloride as auxiliary gelling agent; and 0.001-0.05 wt part of glacial acetic acid as a pH neutralizing agent to the resulting admixture, after cooling the obtained mixture in step i) at 57-63° C.; iii) transferring the resulting admixture to the dipping pan at 57-63° C. after adjusting the viscosity of the mixture obtained in step ii) to be 0.7-1.5 Pa·s at 57° C., forming a pullulan hard capsule using mold pin, and cooling and drying a pullulan hard capsule using 15-35° C. air for 40-70 minutes; wherein said forming step comprises a) adjusting the temperature of mold pin to 20-25° C., b) dipping the mold pin into the dipping pan at constant velocity, and c) withdrawing the mold pin from the dipping pan at accelerated velocity and subsequently at reduced velocity for 16-18 seconds.

Further, the present invention also relates to a pullulan hard capsule having improved film properties prepared by said process, wherein the dissolution profile of acetaminophen at 30 minutes shows more than 70 wt % of dissolution in purified water (pH 7.0) according to the paddle method of dissolution test in Korean pharmacopoeia 10th Edition.

The present invention can be explained in detail as follows.

Pullulan as base material of the present invention has following characteristics, such as, a number of hydroxyl group (—OH) in a molecule, high tackiness and adhesiveness due to its high viscosity, and/or high surface tension. Therefore, it is difficult to maintain a proper film distribution and thickness at the time of forming the hard capsules. Further, following characteristics of pullulan can cause the problems for manufacturing pullulan hard capsules.

First, the difficulty of picking up the solution on the mold pins at the time of dipping and withdrawing the mold pin can cause the problem for adjusting the proper film distribution and thickness.

Secondly, when formed cap and formed body are joined at the Joiner Block, cap and body cannot be properly joined due to high tackiness. Therefore, Semi-docking or Final docking incurred in Joiner Block can cause the improper separation of cap and body, which results in a loss of filled ingredients in the capsules.

Third, the formed capsules also can cause the transferring problem due to high tackiness, when they are continuously transferred through the drums of capsule filling machine, printing machine, visual inspection machine, and/or weight inspection machine.

Fourth, the storage stability problem can also occur due to high tackiness among hard capsules when pullulan hard capsules are stored under high temperature and humidity.

For solving above problems, the present invention has developed a pullulan hard capsule having improved film properties by solving the sticky and/or storage stability problem caused by high tackiness along with the brittleness problem caused by low water content and uneven film strength and/or distribution. Further, a pullulan hard capsule of the present invention can show improved dissolution of filled ingredients with the improved disintegration of pullulan hard capsule shell.

Figure 1:
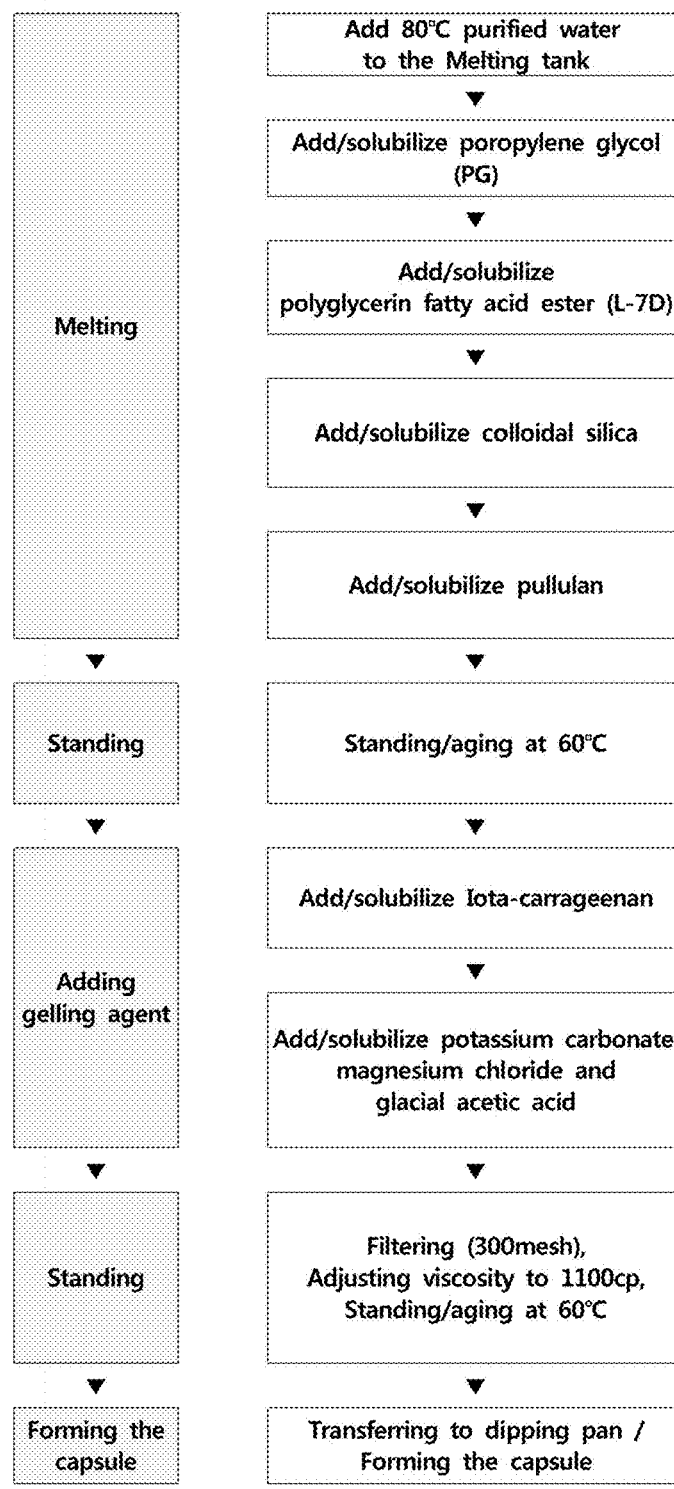
FIG. 1 is a flow diagram showing the preparation steps of pullulan aqueous mixture of the present invention.

FIG. 1 is a flow diagram showing preparation steps of pullulan aqueous mixture of the present invention (Step 1) Melting Step In the melting step, 0.01-0.2 wt part of propylene glycol as plasticizing agent, 0.001-0.02 wt part of polyglycerin fatty acid ester as emulsifying agent, 0.01-0.2 wt part of colloidal silica as viscosity stabilizer, and 18-22 wt part of pullulan have been sequentially added and mixed to the 80 wt part of purified water at 77-83° C., and the mixture has been solubilized. After completing melting step, the pullulan mixture has been allowed to stand at 60° C. for aging.

The preferred weight average molecular weight of pullulan used in this step may be 150-300 kDa, which can provide the viscosity of pullulan aqueous mixture to be 0.7-1.5 Pa·s at 57° C. to improve the film properties for solving sticky and/or brittleness problems. Further, the viscosity of the pullulan may increase according to the increase of weight average molecular weight of pullulan.

The preferred polyglycerin fatty acid ester used in this step is a polyglycerin lauric acid ester having 10-14 HLB value.

Also, the colloidal silica as viscosity stabilizer in this step is preferably a stable spherical particle of fumed silica having 99.0-100.5 wt % of $SiO_2$ content, pH 3.5-5.5 at 4 wt % aqueous solution. Further, the viscosity of the pullulan aqueous mixture can be adjusted to 0.7-1.5 Pa·s at dipping pan temperature (57° C.) using the colloidal silica.

(Step 2) Gelling Agent Addition Step

In this step, after cooling the obtained mixture in Step 1 at 57-63° C., 0.3-1.0 wt part of iota-carrageenan as gelling agent, 0.03-0.3 wt part of potassium carbonate and 0.05-0.3 wt part of magnesium chloride as auxiliary gelling agent; and 0.001-0.05 wt part of glacial acetic acid as a pH neutralizing agent have been sequentially added and solubilized to the resulting admixture.

After completion of this step, the obtained pullulan mixture has been filtered through a 300-mesh sieve. The viscosity of pullulan mixture has been adjusted to 1100 cp, and the pullulan mixture has been allowed to stand at 60° C. for aging.

Iota-carrageenan as gelling agent can concretely gelate the pullulan film of hard capsule in collaborate with $K^+$ cation in potassium carbonate and $Mg^{2+}$ cation in magnesium chloride.

Iota-carrageenan is a kind of polysaccharides derived from seaweed (*chondrus crispus*) polymerized with 2 sugar units of 3,6-anhydrous-D-galactose and D-galactose. Further, a sulfate group at the 2-position of galactose in iota-carrageenan in collaborate with $K^+$ cations in potassium carbonate and $Mg^{2+}$ cations in magnesium chloride can make a concrete gel of iota-carrageenan film.

(Step 3) Capsule Forming Step

After adjusting the viscosity of the mixture obtained in Step 2 to be 0.7-1.5 Pa·s at 57° C., pullulan aqueous mixture has been transferred to the dipping pan at 57-63° C. The temperature of mold pin has been adjusted to 20-25° C. After the mold pin has been dipped into the dipping pan at constant velocity for 16-18 seconds, the mold pin has been withdrawn from the dipping pan at accelerated velocity and subsequently at reduced velocity for forming the pullulan hard capsule.

Figure 2:
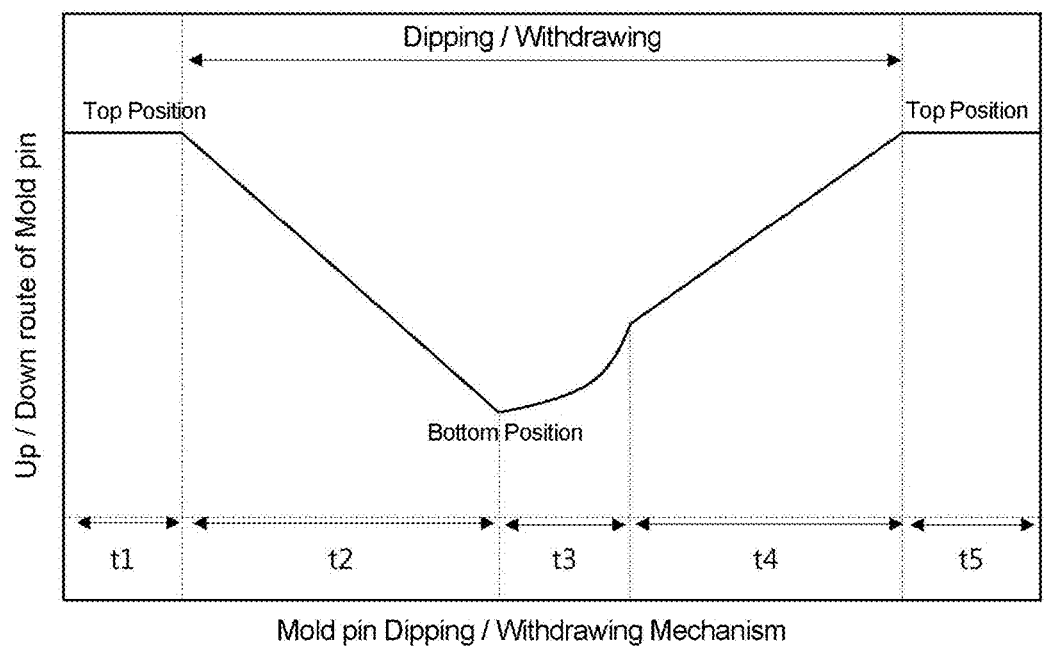
FIG. 2 is a schematic diagram showing the mold pin dipping/withdrawing mechanism when pullulan hard capsule is formed at the mold pin of the present invention.

FIG. 2 is a schematic diagram showing the mold pin dipping/withdrawing mechanism when pullulan hard capsule is formed at the mold pin of the present invention.

In this FIG. 2, t1 represents pin bars transferring for dipping, t2 represents mold pin down at constant velocity, t3 represents mold pin withdrawal at accelerated velocity, t4 represents mold pin withdrawal at reduced velocity, and t5 represents pin bars transferring after withdrawal.

In this step, the circulation rate of the pullulan mixture in the dipping pan has to be adjusted to 18-22 rpm, which is lower than that of HPMC capsules. If the circulation speed is higher than 22 rpm, the level of pullulan mixture becomes higher, which causes the difficulty of mold pin separation from pullulan mixture in dipping pan. On the other hand, if the circulation speed is lower than 18 rpm, the temperature deviation of pullulan mixture increases, which causes the increase of weight deviation of pullulan hard capsule.

In this step, the temperature of dipping pan has been maintained at 55-59° C. If the temperature of dipping pan is higher than 59° C., the film thickness of pullulan hard capsule becomes thinner. On the other hand, if the temperature of dipping pan is lower than 55° C., the film thickness of pullulan hard capsule becomes thicker due to the decreasing flow of pullulan aqueous mixture.

In addition, the temperature of the mold pin has been maintained at 20-25° C. If the temperature of mold pin is higher than 25° C., the film thickness of pullulan hard capsule becomes thinner due to the increasing flow of pullulan mixture. On the other hand, if the temperature of dipping pan is lower than 20° C., the film thickness of pullulan hard capsule becomes elongated due to the decreasing flow of pullulan mixture.

Further, for forming pullulan hard capsules of present invention, the improved dipping/withdrawing mechanism of mold pin has been also developed. The dipping down of the mold pin has been at constant velocity (t2), while the withdrawing of the mold pin has been at accelerated velocity (t3) and subsequently at reduced velocity (t4).

As a result of improving the dipping/withdrawing mechanism, the pullulan hard capsule having uniformed film thickness of the cutting edge and the dome can be obtained.

(Step 4) Cooling and Drying Step

In this step, the formed pullulan hard capsule obtained in Step 3 has been cooled and dried for 40-70 minutes at 15-35° C. Finally, a transparent pullulan hard capsule can be obtained.

In this step, a pullulan hard capsule having improved film properties can be obtained by solving the sticky and/or storage stability problem caused by high tackiness along with the brittleness problem caused by low water content and uneven film strength and/or distribution. Further, the obtained pullulan hard capsule can show improved dissolution of filled ingredients as well as improved disintegration of pullulan hard capsule shell.

Further, a pullulan hard capsule of present invention can show the dissolution profile of acetaminophen at 30 minutes shows more than 70 wt % of dissolution in purified water (pH 7.0) according to the paddle method of dissolution test in Korean pharmacopoeia 10th Edition.

The present invention can be explained more concretely by following Preparation Examples, Comparative Preparation Examples and Examples. However, it should be understood that the Examples are intended to illustrate but not in any manner to limit the scope of the present invention.

(Preparation Example 1) Preparation of Pullulan Hard Capsule of Present Invention (Step 1) Melting Step 40 g of propylene glycol as plasticizing agent, 4 g of polyglycerin lauric acid ester as emulsifying agent, 40 g of colloidal silica as viscosity stabilizer, and 20 Kg of pullulan have been sequentially added and mixed to the 80 L of purified water at 80° C., and the mixture has been solubilized.

(Step 2) Gelling Agent Addition Step

After cooling the obtained mixture in Step 1 at 60° C., 600 g of iota-carrageenan as gelling agent, 80 g of potassium carbonate and 156 g of magnesium chloride as auxiliary gelling agent; and 24 g of glacial acetic acid as a pH neutralizing agent have been sequentially added and solubilized to the resulting admixture.

(Step 3) Capsule Forming Step

After adjusting the viscosity of the mixture obtained in Step 2 to be 1.1 Pa·s at 57° C., pullulan aqueous mixture has been transferred to the dipping pan at 60° C. The temperature of mold pin has been adjusted to 22° C. After the mold pin has been dipped into the dipping pan at constant velocity for 17 seconds, the mold pin has been withdrawn from the dipping pan at accelerated velocity and subsequently at reduced velocity for forming the pullulan hard capsule.

(Step 4) Cooling and Drying Step

The formed pullulan hard capsule obtained in Step 3 has been cooled and dried for 60 minutes at 25° C. Finally, a transparent pullulan hard capsule #0 can be obtained.

(Comparative Preparation Example 1) Preparation of Pullulan Hard Capsule (without Emulsifying Agent and Viscosity Stabilizer)

(Step 1) Melting Step 40 g of propylene glycol as plasticizing agent and 20 Kg of pullulan have been sequentially added and mixed to the 80 L of purified water at 80° C., and the mixture has been solubilized.

(Step 2) Gelling Agent Addition Step

After cooling the obtained mixture in Step 1 at 60° C., 600 g of iota-carrageenan as gelling agent, 80 g of potassium carbonate and 156 g of magnesium chloride as auxiliary gelling agent; and 24 g of glacial acetic acid as a pH neutralizing agent have been sequentially added and solubilized to the resulting admixture.

(Step 3) Capsule Forming Step (Non-Adjustment of Viscosity)

Pullulan aqueous mixture obtained in Step 2 has been transferred to the dipping pan at 60° C. The temperature of mold pin has been adjusted to 22° C. After the mold pin has been dipped into the dipping pan at constant velocity for 17 seconds, the mold pin has been withdrawn from the dipping pan at accelerated velocity and subsequently at reduced velocity for forming the pullulan hard capsule.

(Step 4) Cooling and Drying Step

The formed pullulan hard capsule obtained in Step 3 has been cooled and dried for 60 minutes at 25° C. Finally, a transparent pullulan hard capsule #0 can be obtained.

(Comparative Preparation Example 2) Preparation of pullulan hard capsule (disclosed in WO 2001/07507) (the change of setting system to kappa-carrageenan and potassium acetate) (without emulsifying agent, viscosity stabilizer and pH neutralizing agent)

(Step 1) Melting Step 40 g of propylene glycol as plasticizing agent and 20 Kg of pullulan have been sequentially added and mixed to the 80 L of purified water at 80° C., and the mixture has been solubilized.

(Step 2) Gelling Agent Addition Step

After cooling the obtained mixture in Step 1 at 60° C., 200 g of kappa-carrageenan as gelling agent, 400 g of potassium acetate as auxiliary gelling agent have been sequentially added and solubilized to the resulting admixture.

(Step 3) Capsule Forming Step (Non-Adjustment of Viscosity)

Pullulan aqueous mixture obtained in Step 2 has been transferred to the dipping pan at 60° C. The temperature of mold pin has been adjusted to 22° C. After the mold pin has been dipped into the dipping pan at constant velocity for 17 seconds, the mold pin has been withdrawn from the dipping pan at accelerated velocity and subsequently at reduced velocity for forming the pullulan hard capsule.

(Step 4) Cooling and Drying Step

The formed pullulan hard capsule obtained in Step 3 has been cooled and dried for 60 minutes at 25° C. Finally, a transparent pullulan hard capsule #0 can be obtained.

(Example 1) Capsule Tackiness Test

The 3 kinds of transparent pullulan hard capsules #0 prepared in Preparation Example 1, Comparative Preparation Example 1 and 2 have been used for measuring tackiness of pullulan hard capsules. As a control group, gelatin capsule #0 has been used.

To measure the tackiness, 450 capsules samples have been placed in a measuring container, and then the sample capsules have been transferred using a chute for measuring the number of discharged capsules. If the tackiness of hard capsule increases, the number of discharged capsules has been decreasing. On the other hand, if the tackiness of hard capsule are improved, the number of discharged capsules has been increasing. The results of test have been shown in Table 1.

TABLE 1

|  | Prep. Ex. 1 | Comp. Prep. Ex. 1 | Comp. Prep. Ex. 1 | Control |
|---|---|---|---|---|
| Tackiness (discharged Qty.) | 51 | 32 | 28 | 46 |

The number of discharged capsules prepared in Preparation Example 1 of the present invention has increased more than 1.5 times compared to those of prepared in Comparative Preparation Examples 1 and 2. Further, the tackiness of pullulan hard capsule of the present invention has been improved compared to that of conventional gelatin capsule as control group.

(Example 2) Film Distribution Test

The 3 kinds of transparent pullulan hard capsules #0 prepared in Preparation Example 1, Comparative Preparation Example 1 and 2 have been used for measuring film distribution of pullulan hard capsules. As a control group, gelatin capsule #0 has been used.

For measuring film distribution, the film thickness of the cutting edge part and the dome part have been measured using each 100 sample capsules. The results of test have been shown in Table 2.

TABLE 2

| | Prep. Ex. 1 | | Comp. Prep. Ex. 1 | | Comp. Prep. Ex. 2 | | Control | |
|---|---|---|---|---|---|---|---|---|
| | Cap | Body | Cap | Body | Cap | Body | Cap | Body |
| Cutting edge | 0.104 | 0.098 | 0.096 | 0.092 | 0.102 | 0.094 | 0.105 | 0.100 |
| Dome | 0.117 | 0.105 | 0.101 | 0.093 | 0.100 | 0.104 | 0.120 | 0.110 |

(mm)

The film distribution of capsules prepared in Preparation Example 1 of the present invention has been improved by increasing the thickness of cutting edge and dome compared to those of prepared in Comparative Preparation Examples 1 and 2. Further, the film distribution of pullulan hard capsule of the present invention has been improved as equivalent to that of conventional gelatin capsule as control group.

(Example 3) Capsule Sticky Test

The 3 kinds of transparent pullulan hard capsules #0 prepared in Preparation Example 1, Comparative Preparation Example 1 and 2 have been used for measuring stickiness of pullulan hard capsules. As a control group, gelatin capsule #0 has been used.

For measuring the stickiness of capsule, each 30 sample capsules have been placed in a 90 mm diameter petri dish in the stability chamber at a temperature of 40° C. with a relative humidity of 75% for 3 weeks. The number of sticky capsule has been measured. The results of test have been shown in Table 3.

TABLE 3

| | Prep. Ex. 1 | Comp. Prep. Ex. 1 | Comp. Prep. Ex. 2 | Control |
|---|---|---|---|---|
| Initial (0 day) | 0 | 0 | 0 | 0 |
| 3 weeks later | 1 | 3 | 4 | 1 |

The only 1 number of sticky capsule has been measured 3 weeks later in the chamber in case of the capsule prepared in Preparation Example 1 of the present invention. The same number of sticky capsule also has been measured in gelatin capsule as control. However, the number of sticky capsule prepared in Comparative Preparation Example 1 and 2 is larger than that of pullulan capsule of present invention.

(Example 4) Dissolution Test

Pullulan hard capsules prepared in Preparation Example 1, Comparative Preparation Example 1 and Comparative Preparation Example 2 have been used for testing dissolution profile after filling acetaminophen. The dissolution profile of acetaminophen has been measured in purified water (pH 7.0) for 120 minutes according to the paddle method of dissolution test in Korean pharmacopoeia 10th Edition.

The results of test have been shown in Table 4 and FIG. 3.

TABLE 4

| | | Time(minutes) | | | | | | | | |
|---|---|---|---|---|---|---|---|---|---|---|
| | | 0 | 15 | 30 | 45 | 60 | 75 | 90 | 105 | 120 |
| Dissolution rate of acetaminophen (%) | Prep. Ex. 1 | 0 | 34.2 | 74.5 | 89.6 | 95.4 | 98.7 | 99.5 | 99.7 | 99.8 |
| | Com. Ex. 1 | 0 | 27.5 | 60.7 | 85.4 | 91.7 | 95.0 | 98.8 | 99.0 | 99.7 |
| | Com. Ex. 2 | 0 | 23.4 | 67.5 | 80.3 | 89.2 | 94.1 | 98.7 | 99.2 | 99.7 |

The dissolution rate of capsules prepared in Preparation Example 1 of the present invention showed the highest dissolution rate. On the other hand, the dissolution rate of capsules prepared in Comparative Preparation Example 1 and the dissolution rate of capsules prepared in Comparative Preparation Example 2 as the same product of WO 2001/07507 showed the lower dissolution rate than that of pullulan capsules prepared in Preparation Example 1.

Further, the dissolution profile of acetaminophen of pullulan capsules prepared in Preparation Example 1 at 30 minutes showed 74.5% of dissolution of acetaminophen in purified water (pH 7.0), while the dissolution profiles of acetaminophen of pullulan capsules prepared in Comparative Preparation Examples 1 and 2 at 30 minutes showed 60.7% and 67.5% of dissolution of acetaminophen respectively.

The invention claimed is:

1. A process for preparing a pullulan hard capsule having improved film properties comprising the steps of:
   i) sequentially adding and solubilizing 0.01-0.2 wt part of propylene glycol as plasticizing agent, 0.001-0.02 wt part of polyglycerin fatty acid ester as emulsifying agent, 0.01-0.2 wt part of colloidal silica as viscosity stabilizer, and 18-22 wt part of pullulan to the 80 wt part of purified water at 77-83° C.;
   ii) sequentially adding and solubilizing 0.3-1.0 wt part of iota-carrageenan as gelling agent, 0.03-0.3 wt part of potassium carbonate and 0.05-0.3 wt part of magnesium chloride as auxiliary gelling agent; and 0.001-0.05 wt part of glacial acetic acid as a pH neutralizing agent to the resulting admixture, after cooling the obtained mixture in step i) at 57-63° C.; and
   iii) transferring the resulting admixture to the dipping pan at 57-63° C. after adjusting the viscosity of the mixture obtained in step ii) to be 0.7-1.5 Pa·s at 57° C., forming a pullulan hard capsule using mold pin, and cooling and drying a pullulan hard capsule using 15-35° C. air for 40-70 minutes wherein said forming step comprises a) adjusting the temperature of mold pin to 20-25° C., b) dipping the mold pin into the dipping pan at constant velocity, and c) withdrawing the mold pin from the dipping pan at accelerated velocity and subsequently at reduced velocity for 16-18 seconds.

2. The process for preparing a pullulan hard capsule according to claim 1, wherein the weight average molecular weight of pullulan is 150-300 kDa.

3. The process for preparing a pullulan hard capsule according to claim 1, wherein said iota-carrageenan as gelling agent can concretely gelate the pullulan hard capsule in collaboration with $K^+$ cation in potassium carbonate and $Mg^{2+}$ cation in magnesium chloride.

4. The process for preparing a pullulan hard capsule according to claim 1, wherein said colloidal silica as viscosity stabilizer is used to adjust the viscosity of pullulan aqueous mixture at 57° C. to be 0.7-1.5 Pa·s, which is a stable spherical particle of fumed silica having 99.0-100.5 wt % of $SiO_2$ content, pH 3.5-5.5 at 4 wt % aqueous solution.

5. A pullulan hard capsule having improved film properties prepared by the process according to claim 1, wherein the dissolution profile of acetaminophen at 30 minutes shows more than 70 wt % of dissolution in purified water (pH 7.0) according to the paddle method of dissolution test in Korean pharmacopoeia 10th Edition.

* * * * *